US008000510B2

(12) United States Patent
Boeing et al.

(10) Patent No.: US 8,000,510 B2
(45) Date of Patent: Aug. 16, 2011

(54) METHOD AND CONTROL DEVICE TO CONTROL A SLICE IMAGE ACQUISITION SYSTEM

(75) Inventors: Dieter Boeing, Forchheim (DE); Bernhard Krauss, Burgthann (DE); Stefan Kaepplinger, Jena (DE); Bernhard Schmidt, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/539,687

(22) Filed: Aug. 12, 2009

(65) Prior Publication Data

US 2010/0040268 A1 Feb. 18, 2010

(30) Foreign Application Priority Data

Aug. 12, 2008 (DE) .......................... 10 2008 037 347

(51) Int. Cl.
*G06K 9/00* (2006.01)
*H01L 27/146* (2006.01)
(52) U.S. Cl. .................................. 382/128; 250/370.08
(58) Field of Classification Search .................. 382/128, 382/129, 130, 131, 132, 133, 134; 378/4, 378/21–27, 57, 205, 207, 901; 600/407, 600/410, 411, 425, 427, 729; 128/915, 916, 128/920, 922; 250/370.08, 370.09
See application file for complete search history.

(56) References Cited

U.S. PATENT DOCUMENTS

| 7,453,076 B2* | 11/2008 | Welch et al. ............... 250/492.3 |
| 7,542,792 B2* | 6/2009 | Wollenweber et al. ........ 600/407 |
| 2005/0094765 A1 | 5/2005 | Bijjani et al. |
| 2005/0267348 A1 | 12/2005 | Wollenweber et al. |
| 2006/0198499 A1 | 9/2006 | Spies et al. |
| 2007/0076842 A1 | 4/2007 | Tkaczyk et al. |

FOREIGN PATENT DOCUMENTS

JP 06209928 8/1994

OTHER PUBLICATIONS

Report 05016 CT Scanner Automatic Exposure Control Systems, Medicines and Healthcare Products Regulatory Agency (2005).

* cited by examiner

*Primary Examiner* — Abolfazl Tabatabai
(74) *Attorney, Agent, or Firm* — Schiff Hardin LLP

(57) ABSTRACT

In a method and control device to control a slice image acquisition system, a scan protocol is initially selected from a number of scan protocols, and then an automatic control of the slice image acquisition system (13) ensues on the basis of the selected scan protocol by automatic receipt of previous information regarding the examination subject, automatic synchronization of the previous information with information regarding scan protocol-specific parameters of scan protocols, and automatic selection of the scan protocol, from among the number of scan protocols, that has parameters exhibiting the greatest compatibility with the received previous information according to an established rule.

15 Claims, 3 Drawing Sheets

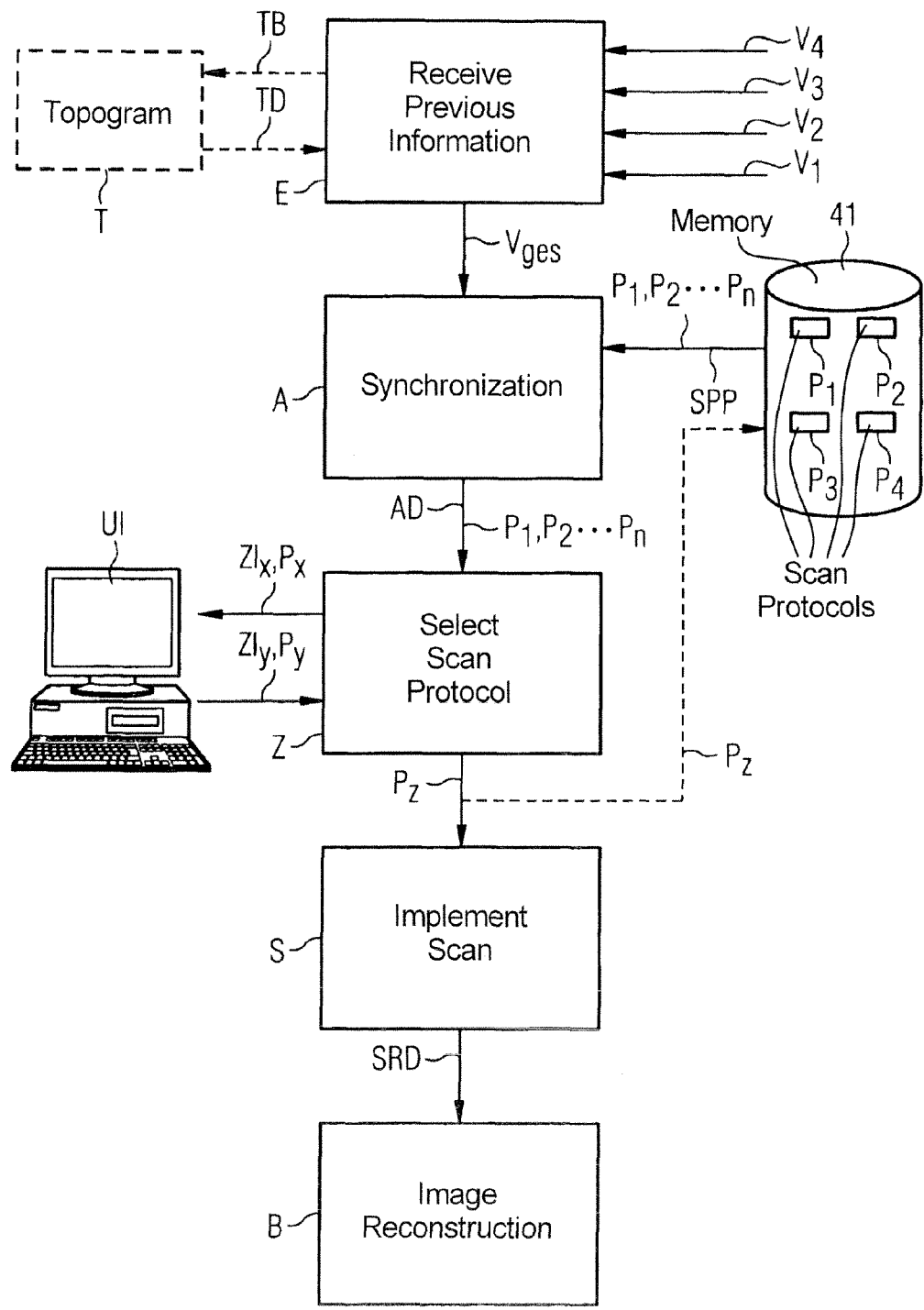

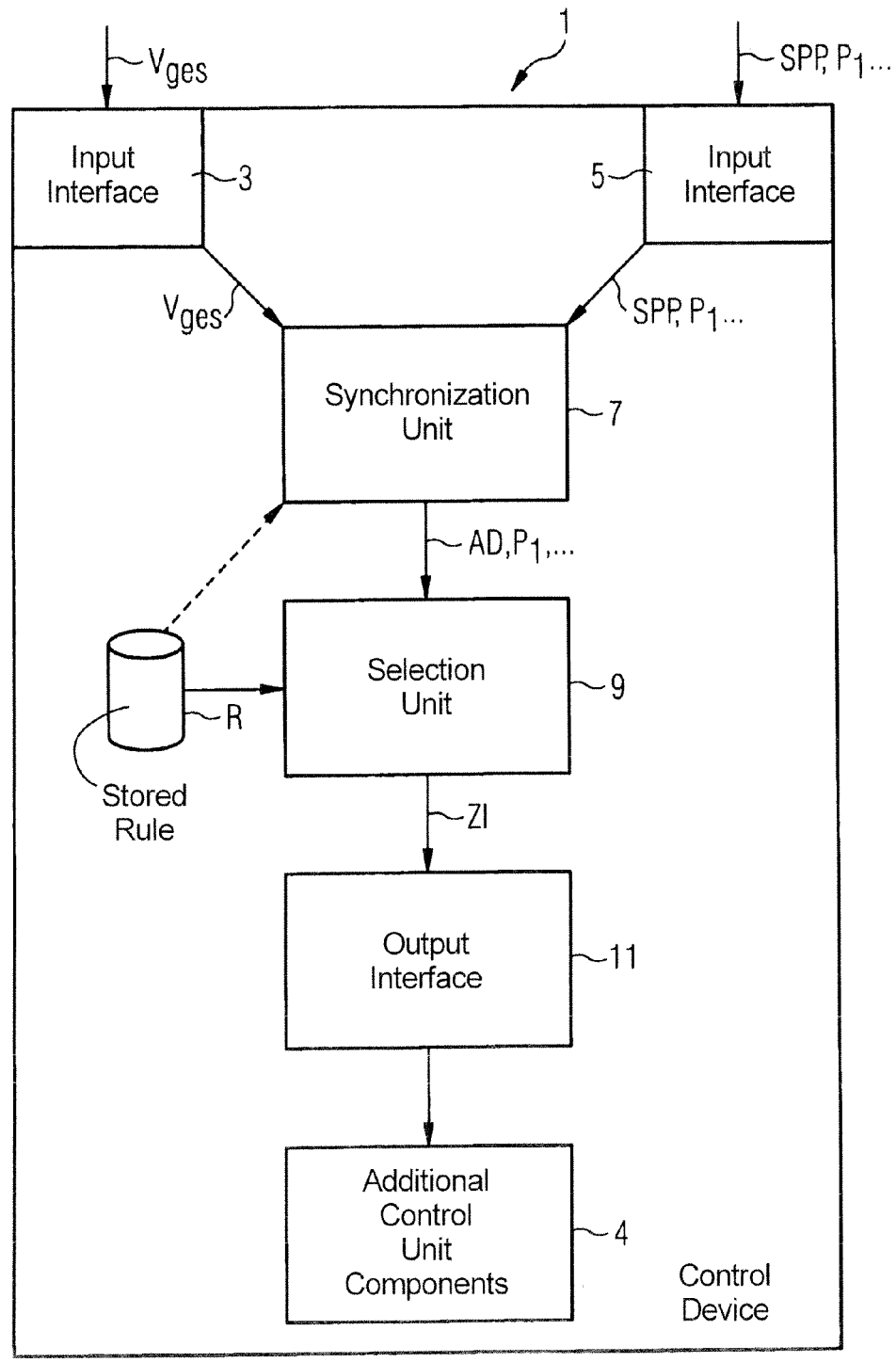

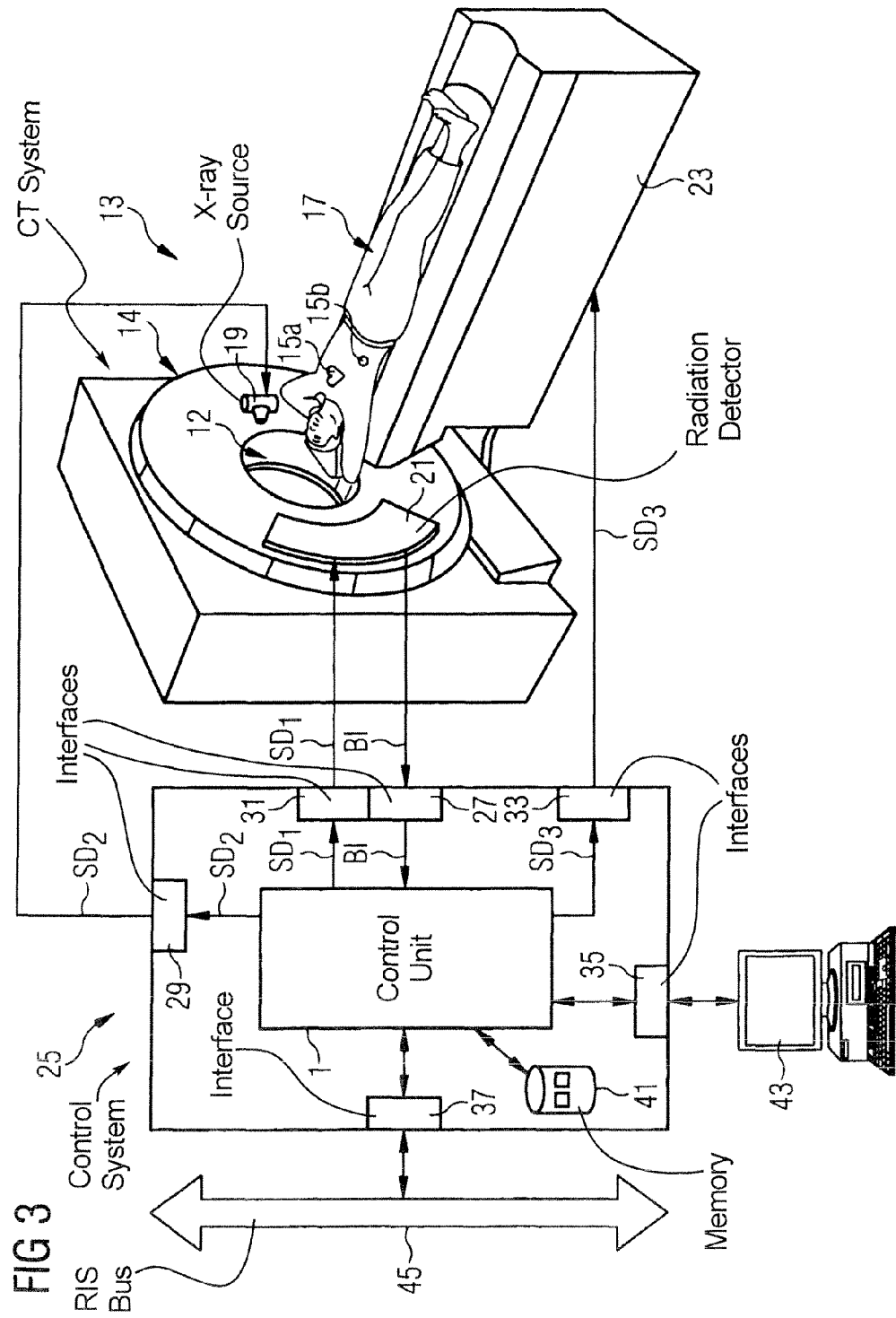

METHOD AND CONTROL DEVICE TO CONTROL A SLICE IMAGE ACQUISITION SYSTEM

BACKGROUND OF THE INVENTION

1. Field of the Invention

The present invention concerns a method to control a slice image acquisition system. Moreover, it concerns a control device to implement such a method.

2. Description of the Prior Art

Scan protocols in slice acquisition systems (such as computed tomography systems, magnetic resonance systems, PET and SPECT scanners and slice image-based image acquisition systems of similar design) serve for the simple control of a scan of specific examination subjects and/or of an image processing of the raw image data generated by the scan. The examination subjects can be positioned in a surrounding housing. The subject can be a human or animal body, but also an inanimate body such as tires or other products that should be scanned for material testing (for instance to examine material inclusions), for example.

Among other things, scan protocol-specific parameters are stored in the scan protocols. In contrast to simple information (such as a title of a scan protocol, for example), scan protocol-specific parameters are technical parameters, i.e. parameters that act as framework data for the control of the slice image acquisition system and/or for the processing of the acquired raw image data. These parameters are typically optimized for specific examination subjects and/or the question that forms the basis of a scan procedure. For example, completely different scan protocol-specific parameters are used for bone examinations within the scope of computed tomography than for the examination of coronary vessels. The parameters for a whole-body examination for prophylactic purposes likewise differ significantly from those of a detailed examination of a specific organ.

The selection of the appropriate scan protocols is presently conducted by the user of a slice image acquisition system. Using the titles of scan protocols, he or she typically selects from a list the scan protocol that is best suited for the examination of the subject to be examined.

Operator errors can enter into a scan protocol over the course of time, because scan protocols can be modified and stored under a different title by users. For example, it can occur that a user randomly selects a scan protocol that, for example, serves for the examination of a bone structure at the knee and incorrectly applies it for examination of a thorax. If the user consequently stores this scan protocol under a new title in which the word "thorax" occurs, a following user will mistakenly assume that this scan protocol is actually suitable for thorax examinations. Conversely, it can occur that a user uses a scan protocol provided for a specific task (for example a protocol for examination of a thorax) as a template for another examination and correspondingly modifies it, for example for examination of a knee. If the user then forgets to change the title of the scan protocol, subsequent users will mistakenly assume that the modified protocol is still a scan protocol for the originally specified application field.

This leads to image quality problems that are caused by the unsuitable parameter settings, or even to completely unusable scan results. Such operating errors due to incorrect or forgotten renamings of scan protocols are not rare in everyday situations, and such incorrectly named scan protocols can only be filtered out with difficulty. Therefore, this negative effect multiples in the course of time, and the result is an increasing uncertainty with regard to the quality of the scan protocols among the examining personnel. However, many operating errors can still creep in even given perfectly maintained data sets, primarily due to incorrect interpretation of existing information regarding scan protocols. There has previously been no reliable method with which such user errors can be precluded.

SUMMARY OF THE INVENTION

It is an object of the present invention to preclude operating errors to the greatest extent possible, and to provide an optimally reliable method for the selection of scan protocols of a slice image acquisition system.

This object is achieved in accordance with the invention by a method to control a slice image acquisition system in which a scan protocol is initially selected from a number of scan protocols, and then an automatic control of the slice image acquisition system ensues on the basis of the selected scan protocol, wherein there ensues automatic receipt of previous information regarding the examination subject, automatic synchronization of the previous information with information regarding scan protocol-specific parameters of scan protocols and automatic selection of the scan protocol from the number of scan protocols whose parameters exhibit the greatest compatibility with the received previous information according to an established rule.

The invention is essentially based on a logical automation. Partial steps of the process can also be implemented in a partially automated manner, for example assisted or initiated by input of a user.

The automation is naturally derived from the given previous information regarding an examination subject, synchronized (calibrated) with information regarding the parameters of scan protocols of that scan protocol that offers the greatest compatibility of the parameters with the received previous information. This automation is based on an established rule in which criteria for the compatibility of previous information and scan protocol-specific parameters are stored. This means that defined scan protocol-specific parameters are respectively associated with specific previous information, for example in a matrix-like database. In the method according to the invention, an automated inquiry asks which scan protocol-specific parameter is associated with a specific piece of previous information. This associated parameter is then synchronized (matched) and classified with the corresponding scan protocol-specific parameters of the scan protocols from the selection of scan protocols, which scan protocols exhibit the greatest agreement between their own parameters and those parameters associated with the previous information.

This procedure can be repeated for every item of received previous information so that overall a ranking of the compatibility of scan protocols with all previous information is created. For this purpose, a weighting can optionally be additionally conducted with regard to the relevance of different items of previous information.

Furthermore, clusters or groups of items of previous information can be formed which can then be associated with a common scan protocol-specific parameter, and/or individual items of previous information or groups of previous information can be associated in turn with groups of scan protocol-specific parameters.

The optimal compatibility of previous information and scan protocol-specific parameters ensures that a user is offered or automatically uses a scan protocol from the outset that is the best possible match for his examination subject and/or his question. In particular, the method precludes a user from initially having to search independently within the scan protocols for that scan protocol that theoretically would be usable for the task at hand.

The object is furthermore achieved by a control device for a slice image acquisition system that is fashioned so that a scan protocol is initially selected in this from a number of scan protocols, and then an automatic control ensues on the basis of the selected scan protocol. The control device at least has an input interface for information regarding scan protocol-specific parameters of scan protocols, a synchronization unit to automatically synchronize the previous information with information regarding scan protocol-specific parameters of scan protocols, a selection unit to automatically select a scan protocol from a number of scan protocols whose parameter, according to an established rule stored in the selection unit or in a memory connected with the selection unit, exhibits the greatest compatibility with the received previous information, and to derive selection information from this selection, and an output interface to forward the selection information.

Such a selection device receives the necessary input values via the two input interfaces for previous information or, respectively, for information regarding scan protocol-specific parameters in order to identify in the synchronization unit and the selection unit, according to the rule stated as an example above, that scan protocol that is best suited for a use on the respective examination subject. The selection information from this selection unit is relayed via an output interface to units for additional processing, for example to control units for the slice image acquisition system and/or for an image processing unit.

The interfaces do not necessarily have to be fashioned as hardware components; rather, they can also be realized as software modules, for example if the previous information can be transferred wholly or partially only in software from a different component already realized on the same apparatus (for example an image reconstruction device for a topography scan or the like) or must be transferred only in software to another component. The interfaces can also consist of hardware and software components, for example a standard hardware interface that is specially configured via software for the concrete use case. Moreover, both interfaces can also be combined in a common interface, for example an input/output interface.

Overall, a majority of the components for realization of the control device in the manner according to the invention can be realized wholly or partially in the form of software modules on a processor, in particular the synchronization unit and the selection unit.

The invention therefore also encompasses a computer-readable medium that can be loaded directly into a processor of a programmable control system, with encoded programming instructions in order to execute all steps of the method according to the invention when the program product is executed by the control system.

In an embodiment of the invention the previous information is the specification of an examination subject-specific goal. In the case of a medical technology scan, this can be the clinical referral request of a referring physician, an instruction for an indication, or a suspicious diagnosis, or information regarding results of previous examinations. In the case of inanimate objects, for example a rubber tire that should be inspected for air inclusions, this can be the requirement that the size and number of air inclusions should be determined.

The selection device according to the invention is fashioned such that, in the assignment unit, a scan protocol is sought that is comparable to the examination subject-specific goal with the scan protocol-specific parameters of scan protocols, and on the basis of this comparison said assignment unit assigns the scan protocol that is best suited for such an examination. The information regarding the examination subject-specific goal is therefore particularly suitable for the method according to the invention because scan protocol-specific parameters can typically be associated with it in a simple manner.

One criterion for such an assignment is, for example whether an examination subject moves significantly (for example a human heart) or rather is immobile (for example a knee that can be kept still by a patient). Among other things, a scan protocol-specific parameter for image acquisition speed can be varied depending on this criterion. For example, in a computed tomography system this affects the revolution speed of the x-ray source and the x-ray detector associated therewith.

Alternatively or in addition to the examination subject-specific goal, additional previous information can be used.

The previous information preferably includes image data from at least one topogram transferred from an imaging system. A topogram is generally an overview exposure of the body of an examination subject or from which initial or preliminary conclusions about position, size or details of the examination subject or of the body of the examination subject can be made, for example. Within the scope of the invention, the topogram can be generated by arbitrary imaging systems. For example, image data from ultrasound examinations or photographic exposures of an examination subject can be used.

In a preferred embodiment of the invention, a topogram is generated in advance by the slice image acquisition system, the image data of the topogram then being used as the previous information. The advantage of the use of a topogram is primarily that a known, common coordinate system of the topogram and of the scan protocol exists, and thus no additional steps are necessary for relating topogram data from other acquisition systems to the scan protocols. Method steps can thus be saved in comparison to the acquisition of topograms with other image acquisition systems. The generation of a topogram by the slice image acquisition system usually is done anyway by default, such that this method step entails no additional outlay before implementation of the method according to the invention.

In particular, an automatic organ detection can be implemented on the basis of a topogram with a suitable subject detection algorithm, the result of which detection (in the form of organ image data) can in turn be fed as previous information into the method according to the invention for control of a slice image acquisition system. Algorithm-based subject detection methods, for example ActiveShapeMode, Active Contour, LevelsetSegmentation or Correlation, as are known to those skilled in the art, can be used for this.

The topogram of which image data are used as previous information is preferably generated as a multiple energy computed tomography image.

Multiple energy computed tomography images have previously been used to implement scan passes from which precision detail image data are acquired that are provided for an additional use by an end user. According to a first variant, this takes place with radiations of different energies, i.e. with x-ray radiation with different energy spectra. In a second variant, x-ray radiation is emitted with a broad energy spectrum and is measured in an energy-selective manner by the detector. "Dual energy" methods with a differentiation between two different energies are already presently used frequently. Compared to methods in which only radiation of one energy is emitted, or the radiation is detected only by one energy integrated by the detector, such multiple energy methods (or, respectively, also "dual energy" methods that are a simple variant of the multiple energy methods) offer the advantage of a distinctly greater usable image contrast. Tissue types that are differentiated in such a manner can in particular be better discriminated from one another given scanning of organic soft tissues in the medical technology field.

Such a multiple-energy method is now implemented to conduct a topogram scan in order to be able to already use the possibility of the higher image contrast within the scope of said scan. For example, this results in the advantage that distinctly more precise tomographic image data are provided than would typically be expected. It is thereby possible to generate separate soft tissue image data and bone data from such tomography image data.

Due to the multiple energy method, it is possible to significantly minimize the overlap of bones and soft tissues in the topogram, or even to remove such overlap entirely. Sought structures can thereby be found significantly more easily and quickly in the image data. For example, the detection of a lung in a conventional (single energy) tomogram with an automatic subject detection method is nearly impossible due to the superimposition of the ribs over the lung structure. By contrast, this is possible without any problems in a soft tissue image generated on the basis of the multiple energy method.

In a similar manner, it is advantageous when soft tissue image data that represent soft tissues and bone data that represent bones can be discriminated from one another from the image data of the tomogram, even given the use of other imaging systems (for example a magnetic resonance tomogram).

Automatic organ detection is therefore advantageously implemented on the basis of, for example, the previously described, pre-differentiated image data (for example a "soft tissue topogram" and a "bone topogram"), the result of which detection can in turn be fed as previous information in the form of organ image data into a control device according to the invention for the implementation of a method according to the invention to control a slice image acquisition system. The subject detection methods described above can be used for this purpose.

The method described in the preceding for identification of subjects by means of a topogram—in which a topogram is generated as a multiple energy computer topogram and soft tissue image data that represent soft tissues and bone image data that represent bones are discriminated from one another on the basis of the multiple energy computer topogram image data and then an automatic subject detection is implemented on the basis of the soft tissue image data and/or the bone image data—is in fact advantageously used to develop the method according to the invention. However, this method can also advantageously be used in other applications.

It can also be advantageous to acquire multiple topograms of the same examination subject from different directions. Subjects can be spatially separated; for example, contrast agent in the intestine can be separated via a lateral acquisition from the underlying spinal column. Moreover, the correct positioning of the patient can be checked given the acquisition of the topograms via the tomography system, for example. In particular, CT systems can also simultaneously acquire such topograms when either a CT system with multiple tubes is used or a single tube is activated with simultaneous table feed in only the required directions (spiral tomogram).

Furthermore, the previous information can advantageously include one or more of the following items of information or data:
  information regarding the position of the examination subject and/or a body surrounding the examination subject,
  information regarding the size and/or the weight of the examination subject or a body surrounding the examination subject, and/or additional examination subject-specific data, and
  scan job data.

The information regarding the positioning of the examination subject or, respectively, of the body surrounding the examination subject can, for example, be information regarding the position and/or alignment of the examination subject with regard to a fixed coordinate system, and/or be simple information regarding a patient, for example whether he is driven head- or feet-first into a tomography scanner. Additional, examination subject-specific data can comprise material information, for example, or the gender of the patient in the case of an animate examination subject.

The more previous information that is provided to the selection device, the more precisely that the scan protocol that is most suitable for a subsequent scan by the slice image acquisition system can be synchronized with the scan protocol-specific parameters.

In principle it is possible to draw upon any type of scan protocol-specific parameters. In a first application field, however, the scan protocol-specific parameters advantageously comprise at least one of the following parameters:
  a radiation source voltage of a radiation source of the slice image acquisition system that is to be applied and
  a power source current that is to be achieved by a radiation source of the slice image acquisition system.

These parameters essentially relate to radiation sources emitting x-rays and/or radioactive radiation, i.e. primarily to use in computer tomography systems. In this case an radiation source can be an x-ray source or a source that emits radioactive radiation. The radiation source voltage applied there or, respectively, the radiation source current that is to be achieved define the radiation dose that is introduced into the examination subject or into a body surrounding the examination subject.

In a second application field, the scan protocol-specific parameters include at least one specification regarding a transmission sequence, for example a pulse sequence of radio-frequency and/or gradient pulses and/or a pulse readout sequence of a field-emitting slice image acquisition system, for example a magnetic resonance tomography apparatus that typically emits different transmission sequences depending on a scan protocol in order to acquire magnetic resonance signals (and thus raw image data).

For all application fields, the scan protocol-specific parameters include, in addition or as an alternative to the aforementioned parameters:
  a reconstruction parameter for an image evaluation and
  a value representing the feed of a subject positioning device.

For example, the quality and the speed of a slice image acquisition is defined by the feed of a subject positioning device as well. The slower the feed, the higher the dose, and therefore the higher the achievable image quality of the image data. Furthermore, this can also possibly be additionally regulated via the revolution speed of a radiation source.

For example, reconstruction parameters for an image evaluation comprise thresholds or similar specifications for filtering the raw image data, or additional parameters that affect the translation of the acquired raw image data into a graphical representation.

The parameters enumerated here vary significantly depending on goals or, respectively, on other previous information regarding the examination subject. They therefore indirectly represent this previous information (if they are matched with it). Inasmuch, an optimally goal-oriented assignment of a scan protocol can be achieved with their help depending on the previous information.

Here the default settings of a typical scan protocol for implementation of what is known as a 4D heart examination in a computer tomograph (i.e. a three-dimensional representation of a heart in a chronological movement sequence) are briefly explained here as an example of scan protocol-specific parameters:

| Parameter | Setting |
| --- | --- |
| Mode | Spiral scan |
| Voltage | 120 kV |
| Effective power charge | 160 mAs |
| Tube current | 533 mA |
| Tube power | 64 kW |
| Initial delay | 0 s |
| Rotation time | 0.33 s |
| Number of collimation surfaces | 64 |
| Areal width of the collimation surfaces | 0.6 mm |
| Positioning device feed per rotation | 6.9 mm |
| Step factor of the feed | 0.18 |
| Gantry inclination | 0° |

The requirements of a 4D heart examination essentially consist of a high image resolution (i.e. precision). In the present case, a scan protocol is therefore selected that controls the computer tomograph so that a spiral scan is implemented with a relatively high radiation charge and a very low table feed. An inclination of the gantry (i.e. of the orbit of the x-ray tube relative to the feed direction of the examination subject) is not provided here, although it is often applied given other organs (for example given the examination of a brain). Since no contrast agent is administered in the case of the heart examination that is intended here, no initial delay is additionally provided as it would be applied if, for example, the contrast agent distribution in a specific phase should be accounted for.

In principle, it is possible to let the method according to the invention run wholly automatically, without interaction by a user. However, the selected scan protocol is advantageously transferred to a user for modification and/or for confirmation, wherein confirmation or, respectively, modification signals are entered by the user via a user interface that is connected with the control device according to the invention, or is integrated into the control device. It can be ensured that the experience of operating personnel that have trained for many years is not ignored, and that an additional fine tuning of the selected scan protocol is enabled if necessary, for example the modification of individual scan protocol parameters. Especially in the medical technology field, it is furthermore necessary that a person trained in medical technology ultimately makes the decision that a scan is implemented with a specific selected scan method. The possibility for confirmation acknowledgment serves for this purpose.

According to a further preferred embodiment of the invention, information regarding the selected scan protocol is stored together with image data acquired in a scan of the slice image acquisition system. In practice, for example, this means that the title (and possibly other information regarding the scan protocol) is added to the image data in the DICOM header (which image data are stored in what is known as the DICOM format (Digital Imaging and Communications in Medicine). For example, these DICOM data can be displayed as well as upon presentation of the image data on monitors or in printouts and are stored as well in the image data file.

BRIEF DESCRIPTION OF THE DRAWINGS

FIG. 1 is a schematic workflow diagram of a method according to the invention.

FIG. 2 is a schematic block representation of a control device according to the invention.

FIG. 3 is a perspective representation of a tomography apparatus with an associated block diagram representation of its control system and additional electronic components.

DESCRIPTION OF THE PREFERRED EMBODIMENTS

FIG. 1 shows a schematic workflow diagram of a method according to the invention. This includes the basic method steps of a receipt E of previous information; a synchronization A of the previous information with information regarding scan protocol-specific parameters of scan protocols; a selection Z of a scan protocol with the greatest compatibility of its parameters with the received previous information; the implementation of a scan S; and the graphical representation B of the respective scan results.

In detail, the method can be implemented as follows:

Previous information (such as Information $V_1$ regarding positioning of an examination subject and/or of a body surrounding the examination subject; Information $V_2$ regarding size of an examination subject and/or of the body surrounding the examination subject; and Information $V_3$ regarding weight of an examination subject and/or of the body surrounding the examination subject; as well as scan job data $V_4$) are received individually or together. Topogram implementation commands TB that serve to control the implementation of a topogram T of the examination subject or, respectively, of a body surrounding the examination subject can be generated with the assistance of this previous information $V_1$, $V_2$, $V_3$, $V_4$. Topogram data TD that can be used as additional information result from such a topogram T. Multiple topograms can thereby also be acquired from different directions. The previous information $V_1$, $V_2$, $V_3$, $V_4$, TD are, for example, bundled together and relayed as previous information $V_{ges}$ for synchronization A.

Information SPP regarding scan protocol-specific parameters from scan protocols $P_1$, $P_2$, $P_3$, $P_4$ stored in a memory 41 enter into the synchronization A. Synchronization data AD result from the synchronization A, from which it can be determined which scan protocol $P_x$ possesses the greatest compatibility of its parameters with the received previous information $V_{ges}$ so that this selected scan protocol $P_x$ is selected in the following for a scan S.

The selection information $ZI_x$ that are generated in this manner or, respectively, the associated scan protocol $P_x$ can be output to a user via a user interface UI for confirmation acknowledgment or, respectively, modification. To confirm or modify a protocol, the user returns selection information $ZI_y$, or, respectively, a confirmed or, respectively, modified scan protocol $P_y$. The selection information $ZI_y$ can also be a simple confirmation signal of the user, such that the originally selected scan protocol $P_x$ remains selected. A final, selected or modified scan protocol $P_z$—this normally corresponds either to the original, automatically selected scan protocol $P_x$ or a scan protocol $P_y$ modified by a user—is provided for the scan S and, if necessary, is relayed to the memory 41 for storage. As a result, raw scan image data acquired in the scan S are relayed for image processing B and there are processed according to the reconstruction parameters of the selected scan protocol $P_z$. Information regarding the selected scan protocol $P_z$ can also be stored with the image data so generated and, for example, be specified as well in a DICOM header.

FIG. 2 shows an exemplary embodiment of a control device 1 according to the invention in a block diagram. In addition to the additional components 4 for controlling a slice image acquisition system, it comprises two input interfaces 3, 5 and one output interface 11. The first input interface 3 serves for the receipt of previous information $V_{ges}$ while the second input interface 5 serves for the receipt of information SPP regarding scan protocol-specific parameters of scan protocols $P_1, P_2, \ldots P_n$ as well as the receipt of these scan protocols $P_1, P_2, \ldots P_n$ themselves. This input is fed into a synchronization unit 7 for synchronization A. The synchronization unit 7 generates from this synchronization data AD that are relayed to a selection unit 9 together with the scan protocols $P_1, P_2, \ldots P_n$, which selection unit derives from these selection information ZI that are relayed via the output interface 11 to the additional components 4 of the control unit. To implement the selection Z and, if necessary, the synchronization A, the selection unit 9 and, if necessary, the synchronization unit access a stored rule R that establishes which scan protocol-specific parameters are associated with which previous information and, if necessary, how the previous information are to be weighted in terms of their importance.

The remaining workflow of the method described in connection with FIG. 1 is controlled via the additional components 4, which include (for example) an output interface for relaying control commands to a tomography apparatus and/or to an image processing unit.

A slice image acquisition system 13 in the form of a computed tomography system 14 is shown in FIG. 3. It is connected with an electronic control system 25. The computed tomography (CT) system 14 essentially comprises: an examination subject positioning unit 23 that is executed in the form of a patient table; and an examination chamber 12 around which are annularly arranged a gantry 14 with an x-ray source 19 and a sensor unit 21 situated opposite on the x-ray source 19 on the revolution track; wherein the x-ray source 19 and the sensor unit 21 are arranged rotating on the gantry 14. The patient table 23 here can be driven into the examination chamber 12; alternatively, it is also possible to move the gantry together with its housing in the direction of the patient table 23. A body 17 of a patient is borne on the patient table 23. Two of its organs are defined as examination subjects: the heart 15*a* and the kidney 15*b*.

The control system 25 is used to implement a tomography scan with the aid of the computer tomograph 13. The control system 25 comprises input or, respectively, output interfaces 27, 29, 31, 33, 35, 27 via which control data $SD_1$, $SD_2$, $SD_3$ are output or, respectively, image information BI are received. The control system 25 furthermore comprises a central control device 1 according to the invention that is arranged on a processor, and a scan protocol memory 41 connected with this. The control device 1 here is represented only as a single block; however, it in particular comprises all components that have already been explained in connection with FIG. 2. It generates control data $SD_1$, $SD_2$, $SD_3$ to control the computer tomograph 13. Control data $SD_1$ to control the sensor unit 21 are sent out via the output interface 31. Image information BI from the sensor unit 21 arrive in the control unit 1 via the input interface 27. This furthermore generates control data $SD_2$ that are relayed via the output interface 29 to the x-ray source 19 to control the same. Additional control data $SD_3$ proceed via the output interface 33 to the examination subject positioning unit 23, whereby its feed is controlled.

The control device 1 is connected with a terminal 43 via an output interface 35. Selection and control information can hereby be input and output in the interaction with a user. Among these are the selected scan protocols $P_x$ (see FIG. 1). A user can confirm or, respectively, modify the scan protocol selection via the graphical user interface of the terminal 43 and have it visualized if necessary. With the use of the control device 1 it is possible to automatically select the scan protocol $P_x$, which can be derived on the basis of previous information $V_{ges}$ that are in turn fed (among other things) into the control device 1 via the terminal 43.

A second output interface 37 is linked with a bus 45 of a radiological information and imaging system (RIS). For example, image data, image processing commands and additional information that should be supplied for a post-processing, storage or forwarding to additional image data users can be relayed via the output interface 37.

Only selected components of a control system 25 and of the computer tomograph that are particularly suitable for clarification of the invention are shown in FIGS. 2 and 3. Naturally, both apparatuses still comprise a plurality of additional functional components.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to control a slice image acquisition system, comprising the steps of:

for an examination subject who is to undergo a scan in a slice image acquisition system, automatically importing into a processor information associated with said examination subject that is relevant to said scan;

from said processor, accessing a plurality of electronically stored scan protocols, each of said scan protocols comprising protocol-specific parameters that serve to control implementation of a scan by said slice image acquisition system;

in said processor, automatically matching said previously-acquired information with information describing the respective protocol-specific parameters of the respective electronically stored protocols; and in said processor, automatically selecting a scan protocol, from among said plurality of electronically stored scan protocols, that has protocol-specific parameters that, as a result of said matching, exhibit a highest compatibility with said information according to a predetermined rule that is stored in and used by said processor, and making the automatically selected scan protocol available at an output of the processor for implementing scan of said examination subject with said slice image acquisition system.

2. A method as claimed in claim 1 comprising employing, as said information, information specifying a goal of said scan of said examination subject that is specific to said examination subject.

3. A method as claimed in claim 1 comprising employing, as said information, image data representing a topogram of the examination subject generated by an imaging system.

4. A method as claimed in claim 1 comprising selecting said information from the group consisting of information describing positioning of the examination subject in the image acquisition system, information describing positioning of a body part of the examination subject in the slice image acquisition system, information describing a size of the examination subject, information describing a weight of the examination subject, and information describing the scan that the examination subject is to undergo in the slice image acquisition system.

5. A method as claimed in claim 1 comprising selecting said protocol-specific parameters from the group consisting of a radiation source voltage of a radiation source of the slice image acquisition system that is to be applied to implement the scan of the examination subject in the slice image acquisition system, and a power source current of said radiation source.

6. A method as claimed in claim 1 wherein said protocol-specific parameters describe a pulse sequence used to activate electromagnetic fields in said slice image acquisition system during a scan.

7. A method as claimed in claim 1 comprising selecting said protocol-specific parameters from the group consisting of information describing feed of the examination subject on a subject positioning device during a scan in the slice image acquisition system, and reconstruction parameters for reconstructing an image from image data acquired by said slice image acquisition system from the scan of the examination subject, and parameters describing evaluation of said image.

8. A method as claimed in claim 1 comprising:
prior to implementing the scan of the examination subject in said slice image acquisition system, generating a topogram of the examination subject with the slice image acquisition system; and
using said topogram as said information.

9. A method as claimed in claim 8 comprising generating said topogram as a multiple energy topogram.

10. A method as claimed in claim 9 comprising, from image data representing said topogram, generating separate images respectively representing soft tissue in said examination subject and soft tissues and bone structures in said examination subject.

11. A method as claimed in claim 10 comprising, in said processor, implementing an automatic organ detection algorithm using at least one of said images, to identify a detected organ in the examination subject from said topogram, and using said detected organ information as said previously-acquired information, and calibrating the automatically selected scan protocol dependent on the detected organ information.

12. A method as claimed in claim 1 comprising making a description of the automatically selected scan protocol available to an operator of the slice image acquisition system for modification or confirmation of the automatically selected scan protocol prior to implementing the scan of the examination subject using said automatically selected scan protocol.

13. A method as claimed in claim 1 comprising electronically storing information describing the automatically selected scan protocol together with image data acquired in the scan of the examination subject with the slice image acquisition system using the automatically selected scan protocol.

14. A control device to control a slice image acquisition system, comprising:
a processor;
an input interface to said processor configured to import information into said processor for an examination subject who is to undergo a scan in a slice image acquisition system, said information being associated with said examination subject and being relevant to said scan;
a memory accessible from said processor, in which a plurality of scan protocols are stored, each of said scan protocols comprising protocol-specific parameters that serve to control implementation of a scan by said slice image acquisition system;
said processor being configured to access said memory and automatically match said previously-acquired information with information describing the respective protocol-specific parameters of the respective electronically stored protocols; and
said processor being configured to automatically select a scan protocol, from among said plurality of electronically stored scan protocols, that has protocol-specific parameters that, as a result of said matching, exhibit a highest compatibility with said information according to a predetermined rule that is stored in and used by said processor, and to make the automatically selected scan protocol available at an output of the processor for implementing scan of said examination subject with said slice image acquisition system.

15. A non-transitory computer-readable medium encoded with programming instructions to control a slice image acquisition system, said programming instructions causing a processor of said system to:
for an examination subject who is to undergo a scan in a slice image acquisition system, automatically import into the processor information associated with said examination subject that is relevant to said scan;
access a plurality of electronically stored scan protocols, each of said scan protocols comprising protocol-specific parameters that serve to control implementation of a scan by said slice image acquisition system;
automatically match said previously-acquired information with information describing the respective protocol-specific parameters of the respective electronically stored protocols; and
automatically select a scan protocol, from among said plurality of electronically stored scan protocols, that has protocol-specific parameters that, as a result of said matching, exhibit a highest compatibility with said previously-acquired information according to a predetermined rule that is stored in and used by said processor, and make the automatically selected scan protocol available at an output of the processor for implementing scan of said examination subject with said slice image acquisition system.

* * * * *